US006197322B1

(12) United States Patent
Dutkiewicz et al.

(10) Patent No.: US 6,197,322 B1
(45) Date of Patent: Mar. 6, 2001

(54) ANTIMICROBIAL STRUCTURES

(75) Inventors: Jacek Dutkiewicz, Appleton; Kurt James Bevernitz, Neenah; Linda Susan Huard; Jian Qin, both of Appleton; Tong Sun, Neenah; Palani Raj Ramaswami Wallajapet, Wauwatosa, all of WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 08/996,485

(22) Filed: Dec. 23, 1997

(51) Int. Cl.⁷ .............................. A01N 25/34; A01N 25/08
(52) U.S. Cl. ....................... 424/412; 424/404; 424/405; 424/409
(58) Field of Search .................... 424/404, 405, 424/409, 412, 414

(56) References Cited

U.S. PATENT DOCUMENTS

| | | | |
|---|---|---|---|
| 4,326,532 | 4/1982 | Hammer | 128/349 R |
| 4,979,959 | 12/1990 | Guire | 623/66 |
| 5,308,663 | * 5/1994 | Nakagawa | 428/34.2 |
| 5,334,388 | 8/1994 | Hoang et al. | 424/402 |
| 5,378,472 | 1/1995 | Muzzarelli | 424/445 |
| 5,432,000 | * 7/1995 | Young, Sr. | 428/372 |
| 5,494,744 | 2/1996 | Everhart et al. | 427/337 |
| 5,498,478 | 3/1996 | Hansen et al. | 428/372 |
| 5,541,233 | 7/1996 | Roenigk | 521/54 |
| 5,582,644 | 12/1996 | Gaddis et al. | 118/303 |
| 5,599,916 | * 2/1997 | Dutkiewicz | 536/20 |
| 5,618,622 | 4/1997 | Gillberg-Laforce et al. | 428/357 |
| 5,652,049 | * 7/1997 | Suzuki | 442/281 |

OTHER PUBLICATIONS

Derwent World Patent Database abstract of JP 5–044,165 A: Description of Unitika Ltd (NIRA), "Antibacterial, Mildew–Proof, And Deodorant Long Fibre For Nonwoven Fabric.", 1993.

Derwent World Patent Database abstract of JP 3–215,533 A: Description of Katakura Chikkarin Co Ltd (KATA–N), "Highly Hydrophilic Polymeric Moulding For Clothes, Etc.", 1991.

Good, Robert J. and Robert J. Stromberg, Editors, Surface and Colloid Science–Experimental Methods, vol. II, Plenum Press, 1979, pp. 31–91.

* cited by examiner

*Primary Examiner*—Carlos A. Azpuru
(74) *Attorney, Agent, or Firm*—Gregory E. Croft

(57) ABSTRACT

Certain antimicrobial agents, particularly chitosan- or chitin-based polymers, exhibit increased antimicrobial activity when coated onto the surface of a hydrophobic material such as polypropylene. When applied to the surface of a polypropylene nonwoven fabric, for example, the resulting material can be used for diaper liners to reduce odors and promote skin wellness.

14 Claims, No Drawings

ANTIMICROBIAL STRUCTURES

BACKGROUND OF THE INVENTION

The use of antimicrobial agents to prevent or retard the growth of bacteria finds applicability in a wide variety of applications in the medical and personal care fields. Some of these applications involve combining an antimicrobial agent with a solid surface. In such cases, it is necessary to attach an antimicrobial agent to the solid surface while maintaining the antimicrobial activity of the antimicrobial agent. Unfortunately, in so doing the antimicrobial activity of the antimicrobial agent can be reduced in the process, rendering the resulting material insufficiently effective.

Hence there is a need for a coated antimicrobial material which exhibits high antimicrobial activity. Such materials could be useful for certain components of personal care articles, such as diaper liners and the like.

SUMMARY OF THE INVENTION

It has now been discovered that certain antimicrobial agents, such as chitosan and other chitin-based materials, when thinly coated onto a substrate having a hydrophobic surface, exhibit antimicrobial activity which is even greater than the activity of the antimicrobial agent alone. In general, the increase in microbial activity can be about 10 percent or greater, more specifically about 50 percent or greater, still more specifically about 100 percent or greater, still more specifically about 200 percent or greater, and most specifically from about 10 to about 500 percent. As used herein, the term "antimicrobial" includes sequestering or immobilizing microorganisms such that their numbers within a suspension medium are reduced, even though the microorganisms may not be killed.

Hence, in one aspect the invention resides in a method for making an antimicrobial structure comprising coating a hydrophobic surface of a solid substrate with a chitosan material, wherein the amount of the chitosan material is from about 0.0005 to about 2.5 grams per square meter on a solids basis. More specifically, the method can include the steps of (1) preparing a solution or suspension containing the chitosan material; (2) coating the solution or suspension onto a hydrophobic surface of a solid substrate; (3) drying the coated substrate; and (4) optionally post-treating the dried structure to insolubilize the chitosan material.

In another aspect, the invention resides in an anitmicrobial structure comprising a solid substrate having a hydrophobic surface, said hydrophobic surface having a coating of a chitosan material of from about 0.0005 to about 2.5 grams per square meter.

In another aspect, the invention resides in a personal care garment, such as a diaper, incontinent garment, feminine pad and the like, comprising a body-side liner, a liquid impervious backsheet, and an absorbent core in between, wherein the body-side liner comprises a polypropylene nonwoven fabric having a coating of a chitosan material of from about 0.0005 to about 2.5 grams per square meter.

The antimicrobial effectiveness of the coated antimicrobial structure appears to be at least partly dependent upon the hydrophobicity of the surface of the substrate and the thickness or amount of the coating. In general, as the hydrophobicity of the surface of the base polymer increases and the thickness of the coating decreases, the effectiveness of the antimicrobial structure is increased. While not wishing to be bound by any particular theory, it is believed that when coating a chitosan material onto a hydrophobic surface of a substrate such as polypropylene, for example, the hydrophobic surface of the polymer attracts the hydrophobic segments (—C—C—)$_n$ and repels the hydrophilic segments (—NH$_2$) of the chitosan material. This results in a structure in which most of the hydrophobic segments of the coated chitosan material (which are also the non-functional segments in terms of antimicrobial properties) are aligned towards the interface between the chitosan material coating and the polymeric substrate. At the same time, most of the hydrophilic segments of the coated chitosan material (which are also the functional segments in terms of antimicrobial properties) are outwardly aligned at the surface of the structure. Such a structure, which has most of the functional groups exposed on the surface, has enhanced antimicrobial properties. The optimal structure would have 100 percent of the functional segments on the outer surface of the coating. Since only the surface portion of the coating contributes to the antimicrobial properties of the composite structure, thinner coatings are more effective. As the coating thickness increases, the interaction between the hydrophobic segments of the chitosan material and the hydrophobic substrate decreases, thereby decreasing the otherwise preferential outward orientation of the hydrophilic segments.

For purposes herein, the term "hydrophobic" means a material having a contact angle of water in air of 90 degrees or greater. In contrast, the term "hydrophilic" refers to a material having a contact angle of water in air of less than 90 degrees. For purposes of this application, contact angle measurements are determined as set forth in "Surface and Colloid Science—Experimental Methods", Vol. II, Robert J. Good and Robert J. Stromberg, Ed. (Plenum Press, 1979).

For purposes herein, the term "chitosan material" means chitosans, modified chitosans (i.e., carboxymethyl chitins/chitosans) and chitosan salts. Such materials can have a wide range of molecular weights. In general, chitosan materials having very high molecular weights and high charge densities have a high viscosity, which may prohibit the formation of the desired thin and even coating layer on the base material, or which may require high dilution with an appropriate solvent in order to process them, either of which situations may be not economical on a commercial scale. On the other hand, if the molecular weight of the chitosan material is too low, it may be difficult to retain the chitosan material on the surface of the substrate, at least in those instances where a water soluble chitosan material is used. To balance desirability of low cost and high substrate retention (low washability), it is suggested that the weight average molecular weight of the chitosan material be from about 1,000 to about 10,000,000, more specifically from about 2,000 to about 1,000,000, still more specifically from about 3,000 to about 800,000, and most specifically from about 5,000 to about 500,000.

A suitable amount of the chitosan material, for purposes of this invention, can be from about 0.0005 to about 2.5 grams per square meter, more specifically from about 0.001 to about 1 gram per square meter, and still more specifically from about 0.005 to about 0.01 gram per square meter. Alternatively, the amount of the chitosan material can be expressed as a dry weight percent of the substrate to which it is applied. Such amounts can be from about 0.01 to about 10 weight percent, more specifically from about 0.1 to about 5 weight percent, and still more specifically from about 1 to about 5 weight percent.

Suitable solid substrates include, but are not limited to, particulates, filaments, films, foams, fibers, agglomerates, nonwovens and fabrics of various polymers. Generally, the physical form having the larger surface area is preferred if possible. Suitable polymers include hydrophobic polymers such as polyethylene, polypropylene, polyester, polyvinyl chloride, polyvinylidene chloride, polystyrene, polyesters, polyamides, polyimides, and copolymers and mixtures of the same. However, even hydrophilic polymers can form a hydrophobic surface if specially treated. For example, polyacrylic acid is a hydrophilic polymer due to the presence of carboxylic acid groups (—COOH). However, the surface of the polyacrylic acid can be very hydrophobic if the solution of the polymer is dried in hot air. That is because the hot air in nature is hydrophobic relative to water which attracts, in the drying process, the hydrophobic segments (—C—C—)$_n$ of the polyacrylic acid stay on the surface and at the same time repels the hydrophilic segments (—COOH) of the polymer away from the surface.

In preparing to coat the substrate using a coating solution or suspension comprising the chitosan material(s), water is generally the preferred solvent or carrier due to its low cost and non-hazardous nature. The concentration of the chitosan material can be from about 0.1 to about 60 weight percent, more specificaly from about 0.5 to about 50 weight percent, and more specifically from about 1 to about 30 weight percent. Particular product applications may require the use of one or more co-solvents, which can include, but are not limited to, methanol, ethanol, acetone, isopropyl alcohol, ethylene glycol, glycerol, and the like.

When the chitosan material is not soluble in the solvent, it can be made as a suspension for coating. In such a situation, the chitosan material must be first prepared into a form which possesses a huge surface area in order to deliver the desired antimicrobial properties. One example of such a form is, but is not limited to, a chitosan micron powder having a particle diameter of from about 0.1 to about 80 microns. Besides having antimicrobial properties, another benefit of using a large surface area micron powder is to enhance the adhesion of the chitosan material to the substrate.

If the adhesion of the chitosan material to the substrate is a concern, additional adhesive material can be added into either the solution or the suspension. Such adhesive material should not be reactive to but compatible with the chitosan material so that it does not have any significant effect of reducing the antimicrobial properties.

In some end-use applications, the coated materials of this invention may have to be exposed to an aqueous solution multiple times. One such example is the use of the coated material as a top layer (close to the skin) in a diaper. Since multiple urine insults are expected, it is important to prevent the chitosan material from being washed away from the top layer. One way to reduce washability of the coating agent is to use one or more crosslinking agents to insolubilize or bind the chitosan material to the substrate. Crosslinking agents suitable for use in the present invention are generally soluble in the solvent used for dissolving the chitosan material and do not substantially reduce the antimicrobial properties. One suitable crosslinking agent is an organic compound having at least two functional groups or functionalities capable of reacting with active groups located on the chitosan materials. Examples of such active groups include, but are not limited to, carboxyl (—COO$^-$), carboxylic acid (—COOH), amino (—NH$_2$), or hydroxyl (—OH) groups. Examples of such suitable crosslinking agents include, but are not limited to, diamines, polyamines, diols, polyols, polycarboxylic acids, polyoxides, and the like.

One way to introduce a crosslinking agent into the chitosan material solutions is to mix the crosslinking agent with the chitosan material during preparation of the solution. Another suitable crosslinking agent comprises a metal ion with more than two positive charges, such as $Al^{3+}$, $Fe^{3+}$, $Ce^{3+}$, $Ce^{4+}$, $Ti^{4+}$, $Zr^{4+}$ and $Cr^{3+}$. In the case of cationic polymers, polyanionic substances are also suitable crosslinking agents. Examples are sodium polyacrylate, carboxymethylcellulose, polyphosphate, and the like. Since the cations on the chitosan material possess antimicrobial properties, it is not preferred to use a crosslinking agent reactive to the cations unless no alternative crosslinking agent is available.

When using crosslinking agents for purposes of this invention, a suitable amount of crosslinking agent is from about 0.001 to about 30 weight percent based on the dry weight of the chitosan material, more specifically from about 0.02 to about 20 weight percent, more specifically from about 0.05 to about 10 weight percent, and still more specifically from about 0.1 to about 5 weight percent.

After the coating step, a drying process may be necessary to remove any solvent used to dissolve or disperse the chitosan material. The drying temperature is important because hot air is hydrophobic and may reduce the number of functional segments on the surface of the coating layer. In general, a relatively low drying temperature is preferred. Suitable temperatures can be from about 40° C. to about 150° C., more specifically from about 40° C. to about 100° C., and still more specifically from about 40° C. to about 80° C. If a high temperature is needed and the hydrophobicity of the hot air is a concern, humidified air can be used. The relative humidity of the hot and humidified air can be from about 30 to about 90 percent, more specifically from about 40 to about 80 percent, more specifically from about 40 to about 70 percent, and still more specifically from about 40 to about 60 percent.

As stated previously, a post treatment may be necessary to induce a crosslinking reaction to occur when a latent crosslinking agent is used. Suitable post treatments include, but are not limited to, heat curing (>40° C.), ultra-violet light exposure, microwave treatment, electron beam radiation, steam or high pressure treatment, organic solvent or humidity treatment, etc.

EXAMPLES

Twelve different samples were prepared in order to illustrate the effectiveness of the chitosan materials of this invention. These samples are summarized below:

| | |
|---|---|
| Sample #1 | 2% chitosan-HCl solution, VNS-608, Mw = 11,000,000, Degree of Acetylation = 0.14 |
| Sample #2 | 35% Na-polyacrylate solution, Mw = 60,000, Degree of Neutralization = 50% |
| Sample #3 | 2% chitosan acetate solution, VNS-608, Mw = 11,000,000, Degree of Acetylation = 0.14 |
| Sample #4 | 2% carboxymethyl cellulose solution, Aqualon CMC-7H3SXF, DS = 0.7, Mw = 1,000,000 |
| Sample #5 | 20% polydiallydimethylammonium chloride solution |
| Sample #6 | Chitosan acetate film (0.3 mm thickness), casting film from Sample #3 |
| Sample #7 | Chitosan sulfate film (0.3 mm thickness), Sample #6 treated with 1% H$_2$SO$_4$, washed/dried |
| Sample #8 | Chitosan film (0.3 mm thickness), Sample #6 treated with 1% NaOH, washed/dried |
| Sample #9 | Polypropylene (PP) spunbond liner (0.50 ounces per square yard; denier of 2 dpf) w/3 wt % chitosan acetate coating (Sample #3 solution) |

-continued

| Sample #10 | PP spunbond liner w/3 wt % chitosan sulfate coating, Sample #9 treated with 1% $H_2SO_4$, washed/dried |
| Sample #11 | PP spunbond liner w/3 wt % chitosan coating, Sample #9 treated with 1% NaOH, washed/dried |
| Sample #12 | PP spunbond liner wo/coating (control) |

SAMPLE PREPARATION

The various samples were prepared as follows:

Sample 1: 18 grams of chitosan (VNS-608 from Vanson Chemical Company Inc., Redmond, Wash.; molecular weight of 11,000,000; degree of acetylation of 0.14) were dispersed in 544 grams of distilled water. To this mixture was added 6.4 milliliters of an aqueous solution of hydrochloric acid having a concentration of 37 percent. The resultant mixture was stirred until the chitosan was dissolved. To this solution was added 37 milliliters of distilled water. The solution was stirred again for 30 minutes and filtered through a Buchner funnel using a polypropylene filter fabric.

Sample 2: 35 grams of sodium polyacrylate (molecular weight of 60,000 and degree of neutralization of 50 percent) were dissolved in 65 grams of distilled water by stirring the mixture until the solution was clear.

Sample 3: 4.5 grams of chitosan (same as that of Sample 1) were dispersed in 185.5 grams of distilled water. To this mixture were added 1.5 milliliters of glacial acetic acid and the resultant mixture was stirred until the chitosan was dissolved. 33.5 milliliters of distilled water was added to the solution and the solution was stirred again for 30 minutes and filtered through a Buchner funnel using a polypropylene filter fabric.

Sample 4: 2 grams of carboxymethylcellulose (CMC-7H3SXF from Aqualon Oil Field Chemicals, Division of Hercules Incorporated, Houston, Tex.; molecular weight of 1,000,000 and degree of substitution of 0.7) was dissolved in 98 grams of distilled water by stirring the mixture until the solution was clear.

Sample 5: About 68 milliliters of 60 percent by weight aqueous solution of diallyldimethylammonium chloride monomer was added to a 500 milliliter conical flask. To this about 132 milliliters of distilled water was added to make a 20 percent solution of diallyidimethylammonium chloride in water. The solution was purged with nitrogen gas for 20 minutes and placed in a shaker water bath maintained at 60° C. After the temperature of the monomer solution reached 60° C., 0.072 grams of potassium persulfate and 0.28 grams of sodium bisulfite was dissolved into the monomer solution to initiate polymerization. The reaction was continued for 24 hours by maintaining the solution at 60° C. After completion of the reaction, the viscous polymer solution was added to 1 liter of acetone to precipitate the polymer. The precipitated polymer was redissolved in 200 milliliters of distilled water and reprecipitated in 1000 milliliters of acetone. The dissolution and precipitation was repeated three times and the recovered polymer was dried at 40° C. About 20 grams of the dried polymer was then dissolved in 80 milliliters of distilled water to make the 20 percent solution of polydiallyidimethylammonium chloride in water.

Sample 6: 10 grams of a chitosan material (VSN-608 from Vanson having a viscosity of 11,400 cps for a 1% solution in 1% acetic acid) was suspended in 2 liters of distilled water and mixed with acetic acid with a molar ratio of chitosan to acetic acid of about 0.9 to 1. After more than 15 hours of mixing time, the chitosan material was completely dissolved. (This solution (0.5% concentration) was used in film casting and nonwoven coating treatments to prepare several of the samples described below). The solution was poured onto a surface treated (non sticky) pan and air dried at room temperature for two days. The dried film was further heat treated at 80° C. for 30 minutes.

Sample 7: The film of Sample 6 was immersed in a large amount of a 1% aqueous sulfuric acid solution for at least 4 hours, washed thoroughly with distilled water and dried at 60° C.

Sample 8: The film of Sample 6 was immersed in a large amount of a 1% aqueous sodium hydroxide solution for at least 4 hours, washed thoroughly with distilled water and dried at 60° C.

Sample 9: Commercial polypropylene spunbond liner taken from a HUGGIES® diaper manufactured by Kimberly-Clark Corporation was dipped into the 0.5% chitosan acetate of solution described in the preparation of Sample 6 and dried at room temperature (most of the chitosan acetate solution on the surface of the liner was removed to achieve an even coating). The dried liner was heat treated at 80° C. for 30 minutes. About 5.5 dry weight percent of the chitosan acetate was estimated to be coated onto the surface of the liner using the weight difference before and after the treatment.

Sample 10: The treated liner of Sample 9 was immersed in a large amount of a 1% aqueous sulfuric acid solution for at least 2 hours, washed thoroughly with distilled water and dried at 60° C.

Sample 11: The treated liner of Sample 9 was immersed in a large amount of a 1% aqueous sodium hydroxide solution for at least 2 hours, washed thoroughly with distilled water and dried at 60° C.

Sample 12: Untreated commercial polypropylene spunbond liner.

ANTIMICROBIAL TESTING OF THE SAMPLES

Examples 1–4

For solution samples(#1–#4): The test is performed by mixing the test solutions with the challenge organisms (*E. coli, S. aureus, P. aeruginosa, C. albicans, A. niger*), incubating at room temperature for 24 hours (up to 48 hours for yeast, and 7 days for molds), and periodically sampling the mixture to determine the number of viable organisms remaining in the test sample. Enumeration of remaining organism in the sampling solution mixture enabled quantitative measurement of antimicrobial activity, as measured by Colony Forming Units (CFUs).

Example 5

For solution sample (#5): For the 20% polydiallydimethylammonium chloride solution, the test was performed by inoculating the test solutions separately with the challenge organisms (*E. coli, S. aureus* and *C. albicans*) and incubating at 31° C. Serial dilutions were performed at time points 0, 6, 30 and 54 hours. *E. coli* and *S. aureus* were enumerated on duplicate plates of 1% tripticase soy agar (TSA) and *C. albicans* was enumerated on duplicate plates of sabouraud dextrose agar.

Examples 6–8

For film samples(#6–#8): Test material was cut in 3 sample weights of 25 mg, 50 mg and 100 mg, and placed in individual wells of 6-well FALCON tissue culture plates. *S. aureus* inoculum was prepared in physiological saline such that the bacterial concentration was fixed at approximately $5\times10^6$ CFU/ml. Inoculum volumes added to pre-weighed samples were: 10 ml for sample #6 (due to the absorbent nature of the material), and 5 ml for samples #7 and #8. Inoculated samples were covered and incubated on a rotating platform set at 100 rpms. Serial dilutions of samples were prepared in letheen neutralizing broth at time points of zero, two and four hours. Viable *S. aureus* recovery was determined by plating the dilutions onto nutrient agar. Controls of straight inoculum (5 ml) were simultaneously evaluated at the designated time points. Antimicrobial activity was determined by sample recovery relative to control recovery. Note: only *S. aureus* was assayed with this method.

Examples 9–12

For coated samples(#9–#12): Test material was cut with a calibrated die cutter into 1⅛ inch disks and weighed prior to analysis. Each test organism (*S. aureus, E. coli, C. albicans*) was washed and resuspended in pH 5 acetate buffer. Organisms were applied to the test material in a volume of 2 $\mu m$ of inoculum per milligram of material. Inoculated organisms were allowed contact incubation times of zero, 3 and 6 hours. The zero time point samples were processed immediately, and the 3 and 6 hour samples were incubated in a sterile, humidified, enclosed 31° C. chamber (approximate skin surface temperature). Samples were processed by placing inoculated disks into 25 milliliters of letheen neutralizing solution and vortexing vigorously for 30 seconds to remove adhering organisms into the surrounding fluid. Serial dilutions of this solution were spread plated onto nutrient agar to recover viable test organisms. Enumeration of organism recovery of samples relative to controls enabled quantitative measurement of antimicrobial activity.

The results of the antimicrobial testing are summarized in the tables which follow:

TABLE 1

Solutions

| Sample # | Organism | CFU's @ t = 0 hr | CFU's @ t = 24 hrs | CFU's @ t = 30 hrs |
|---|---|---|---|---|
| #1 | S. aureus | $1.9 \times 10^7$ | 0 | |
| | P. aeruginosa | $4.9 \times 10^6$ | $1.4 \times 10^5$ | |
| | E. coli | $2.1 \times 10^5$ | 0 | |
| | C. albicans | 0 | 0 | |
| | A. niger | $2.2 \times 10^5$ | $2.4 \times 10^6$ | |
| #2 | S. aureus | $6.3 \times 10^7$ | $4.1 \times 10^7$ | |
| | P. aeruginosa | $6.4 \times 10^6$ | 0 | |
| | E. coli | $1.4 \times 10^7$ | 0 | |
| | C. albicans | $6.3 \times 10^5$ | $1.6 \times 10^4$ | |
| | A. niger | $4.7 \times 10^5$ | $1.3 \times 10^6$ | |
| #3 | S. aureus | $1.7 \times 10^8$ | $1.7 \times 10^7$ | |
| | P. aeruginosa | $4.0 \times 10^5$ | 0 | |
| | E. coli | $3.8 \times 10^5$ | $6.4 \times 10^3$ | |
| | C. albicans | 0 | 0 | |
| | A. niger | $7.7 \times 10^4$ | $4.6 \times 10^5$ | |
| #4 | S. aureus | $7.2 \times 10^7$ | $1.8 \times 10^8$ | |
| | P. aeruginosa | $5.0 \times 10^7$ | $6.5 \times 10^8$ | |
| | E. coli | $4.2 \times 10^7$ | $6.4 \times 10^8$ | |
| | C. albicans | $5.5 \times 10^5$ | $9.4 \times 10^6$ | |
| | A. niger | $8.5 \times 10^5$ | $8.4 \times 10^5$ | |
| #5 | E. coli | $1.64 \times 10^5$ | | 0 |
| | S. aureus | $1.37 \times 10^5$ | | 0 |
| | C. albicans | $1.88 \times 10^5$ | | 0 |

Conclusion: Chitosan hydrochloride (Sample 1) and chitosan acetate (Sample 3) exhibited significantly higher antimicrobial activity than sodium polyacrylate (Sample 2) and carboxymethylcellulose (Sample 4). Polydiallyldimethylammonium chloride (Sample 5) also exhibited high antimicrobial activity.

TABLE 2

Chitosan Films
(*S. aureus* inoculum $5.9 \times 10^6$)

| Sample Wt | Time (hrs) | Sample #6 | Sample #7 | Sample #8 | Control |
|---|---|---|---|---|---|
| 25 mg | 0 | $3.9 \times 10^6$ | $6.1 \times 10^6$ | $7.7 \times 10^6$ | $7.9 \times 10^6$ |
| | 2 | $1.3 \times 10^4$ | $6.4 \times 10^6$ | $5.2 \times 10^6$ | $1.2 \times 10^6$ |
| | 4 | $6.9 \times 10^4$ | $7.9 \times 10^8$ | $2.2 \times 10^6$ | $1.7 \times 10^5$ |
| 50 mg | 0 | $5.0 \times 10^6$ | $5.9 \times 10^6$ | $4.9 \times 10^6$ | $7.9 \times 10^8$ |
| | 2 | $7.1 \times 10^3$ | $5.1 \times 10^6$ | $3.6 \times 10^6$ | $1.2 \times 10^6$ |
| | 4 | $1.4 \times 10^3$ | $5.4 \times 10^6$ | $3.5 \times 10^6$ | $1.7 \times 10^5$ |
| 100 mg | 0 | n/e | $5.5 \times 10^6$ | $6.4 \times 10^6$ | $7.9 \times 10^6$ |
| | 2 | n/e | $9.6 \times 10^6$ | $2.4 \times 10^6$ | $1.2 \times 10^6$ |
| | 4 | n/e | $7.0 \times 10^6$ | $2.9 \times 10^5$ | $1.7 \times 10^5$ |

TABLE 3

Chitosan Coated on Polypropylene Liner

| Organism | Time (hrs) | Sample #9 | Sample #10 | Sample #11 | Sample #12 |
|---|---|---|---|---|---|
| S. aureus | 0 | $8.1 \times 10^6$ | $7.6 \times 10^6$ | $5.7 \times 10^6$ | $8.2 \times 10^6$ |
| (Inoc. $7.3 \times 10^8$) | 3 | $5.6 \times 10^3$ | $8.6 \times 10^5$ | $2.3 \times 10^3$ | $7.3 \times 10^6$ |
| | 6 | $3.0 \times 10^3$ | $4.3 \times 10^5$ | <100 | $2.8 \times 10^5$ |
| E. coli | 0 | $3.0 \times 10^6$ | $4.0 \times 10^6$ | $3.7 \times 10^6$ | $3.7 \times 10^6$ |
| (Inoc. $4.1 \times 10^6$) | 3 | <100 | $4.6 \times 10^4$ | $2.5 \times 10^3$ | $6.8 \times 10^5$ |
| | 6 | <100 | $7.9 \times 10^3$ | <100 | $5.8 \times 10^5$ |
| C. albicans | 0 | $3.9 \times 10^4$ | $8.1 \times 10^4$ | $8.1 \times 10^4$ | $6.3 \times 10^4$ |
| (Inoc. $5.0 \times 10^4$) | 3 | $7.0 \times 10^3$ | $5.2 \times 10^4$ | $1.0 \times 10^4$ | $4.8 \times 10^4$ |
| | 6 | $3.0 \times 10^3$ | $1.3 \times 10^4$ | <100 | $1.7 \times 10^4$ |

Conclusion:
The chitosan acetate (Sample #9), chitosan sulfate (Sample #10) and chitosan (Sample #11) coated on a hydrophobic surface demonstrate antimicrobial activities compared to the control material (Sample #12)

Comparing the antimicrobial activity of Samples 6 vs 9, Samples 7 vs 10 and Samples 8 vs 11, it is surprisingly shown that with respect to *S. aureus*, the antimicrobial activity of the structures of this invention (chitosan coated onto a polypropylene nonwoven fabric) is greater than the antimicrobial activity of the chitosan films alone.

The foregoing examples, given for purposes of illustration, are not to be construed as limiting the scope of this invention, which is defined by the following claims and all equivalents thereto.

We claim:
1. A method for making an antimicrobial structure comprising coating a hydrophobic surface of a solid substrate with a chitosan material and crosslinking the chitosan, wherein the amount of the chitosan material is from about 0.0005 to about 2.5 grams per square meter on a solids basis.
2. The method of claim 1 wherein the amount of the chitosan material is from about 0.001 to about 1 gram per square meter.
3. The method of claim 1 wherein the amount of the chitosan material is from about 0.005 to about 0.01 gram per square meter.
4. The method of claim 1 wherein the substrate is a nonwoven fabric.
5. The method of claim 1 wherein the substrate is a polypropylene nonwoven fabric.
6. The method of claim 1 wherein the chitosan coating is applied to the substrate as an aqueous solution or suspension containing from about 0.1 to about 60 weight percent of the chitosan material.

7. The method of claim 6 wherein the aqueous solution or suspension further comprises a crosslinking agent for binding the chitosan material to the substrate.

8. The method of claim 7 wherein the amount of crosslinking agent is from about 0.001 to about 30 weight percent based on the dry weight of the chitosan material.

9. The method of claim 6 wherein the chitosan coating is dried at a temperature of from about 40° C. to about 150° C.

10. An anitmicrobial structure comprising a solid substrate having a hydrophobic surface, said hydrophobic surface having a coating of a crosslinked chitosan material in an amount of from about 0.0005 to about 2.5 grams per square meter.

11. The antimicrobial structure of claim 10 wherein the amount of the chitosan material is from about 0.001 to about 1 gram per square meter.

12. The antimicrobial structure of claim 10 wherein the amount of the chitosan material is from about 0.005 to about 0.01 gram per square meter.

13. A wet wipe comprising the antimicrobial structure of claim 10.

14. A personal care garment comprising a body-side liner, a liquid impervious backsheet, and an absorbent core in between, wherein the body-side liner comprises a polypropylene nonwoven fabric having a coating of a crosslinked chitosan material of from about 0.0005 to about 2.5 grams per square meter.

* * * * *

UNITED STATES PATENT AND TRADEMARK OFFICE
CERTIFICATE OF CORRECTION

PATENT NO.   : 6,197,322 B1
DATED        : March 6, 2001
INVENTOR(S)  : J. Dutkiewicz et al.

It is certified that error appears in the above-identified patent and that said Letters Patent is hereby corrected as shown below:

Columns 8, 9 and 10,
Beginning at line 4, the following claims should read:

-- IN THE CLAIMS

1.  A method for making an antimicrobial structure comprising coating a hydrophobic surface of a solid substrate with a chitosan material consisting essentially of chitosan and crosslinking the chitosan, wherein the amount of the chitosan material is from about 0.0005 to about 2.5 grams per square meter on a solids basis.

10.  An antimicrobial structure comprising a solid substrate having a hydrophobic surface, said hydrophobic surface having a coating consisting essentially of a crosslinked chitosan material in an amount of from about 0.0005 to about 2.5 grams per square meter.

14.  A personal care garment comprising a body-side liner, a liquid impervious back sheet, and an absorbent core in between, wherein the body-side liner comprises a polypropylene nonwoven fabric having a coating consisting essentially of a crosslinked chitosan material of from about 0.0005 to about 2.5 grams per square meter.

Signed and Sealed this

Twenty-fifth Day of June, 2002

*Attest:*

JAMES E. ROGAN
*Director of the United States Patent and Trademark Office*

*Attesting Officer*

UNITED STATES PATENT AND TRADEMARK OFFICE
CERTIFICATE OF CORRECTION

PATENT NO.   : 6,197,322 B1
DATED        : March 6, 2001
INVENTOR(S)  : J. Dutkiewicz et al.

It is certified that error appears in the above-identified patent and that said Letters Patent is hereby corrected as shown below:

Column 8,
Line 14, delete "$10_8$" and substitute therefor -- $10_6$ --.
Line 20, insert the following immediately following the end of Table 2:

-- Conclusion: Only chitosan acetate (Sample 6) film demonstrates antimicrobial activity. Chiston (Sample 8) and Chiston Sulfate (Sample 7) films do not. Note: Symbol "n/e" means "not evaluated" --.

Signed and Sealed this

Fourteenth Day of January, 2003

JAMES E. ROGAN
*Director of the United States Patent and Trademark Office*